(12) United States Patent
Cronenberg et al.

(10) Patent No.: US 8,556,862 B2
(45) Date of Patent: Oct. 15, 2013

(54) NEEDLE MOUNTING FEATURE FOR ENSURING PROPER RECONSTITUTION SEQUENCE

(75) Inventors: Richard A. Cronenberg, Mahwah, NJ (US); Asif Fayyaz, Paramus, NJ (US); Atul Patel, Wilkes-Barre, PA (US); Matthew D. Sweeney, Bloomfield, NJ (US); Lionel Vedrine, Palo Alto, CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/119,200

(22) PCT Filed: Sep. 18, 2009

(86) PCT No.: PCT/US2009/057483
§ 371 (c)(1),
(2), (4) Date: May 3, 2011

(87) PCT Pub. No.: WO2010/033806
PCT Pub. Date: Mar. 25, 2010

(65) Prior Publication Data
US 2011/0201999 A1    Aug. 18, 2011

Related U.S. Application Data

(60) Provisional application No. 61/192,466, filed on Sep. 18, 2008, provisional application No. 61/192,464, filed on Sep. 18, 2008, provisional application No. 61/192,465, filed on Sep. 18, 2008, provisional application No. 61/192,389, filed on Sep. 18, 2008, provisional application No. 61/192,467, filed on Sep. 18, 2008.

(51) Int. Cl.
*A61M 5/32*     (2006.01)

(52) U.S. Cl.
USPC .......................................................... 604/195

(58) Field of Classification Search
USPC .......................................................... 604/195
See application file for complete search history.

(56) References Cited

U.S. PATENT DOCUMENTS

| | | | |
|---|---|---|---|
| 5,478,323 A | 12/1995 | Westwood et al. | |
| 5,488,946 A | 2/1996 | Calhoun et al. | |
| 5,549,575 A | 8/1996 | Giambattista et al. | |
| 5,584,815 A | 12/1996 | Pawelka et al. | |
| 6,793,646 B1 * | 9/2004 | Giambattista et al. | 604/90 |
| 8,092,419 B2 * | 1/2012 | Matusch | 604/68 |
| 2011/0160676 A1 * | 6/2011 | Liversidge | 604/198 |
| 2012/0078172 A1 * | 3/2012 | Bendek et al. | 604/92 |

FOREIGN PATENT DOCUMENTS

| | | | |
|---|---|---|---|
| EP | 0351541 A1 | | 1/1990 |
| GB | 0815748.9 | * | 8/2008 |
| WO | WO 2010023488 A1 | * | 3/2010 |

\* cited by examiner

*Primary Examiner* — Aarti B Berdichevsky
(74) *Attorney, Agent, or Firm* — Hoffmann & Baron, LLP

(57) ABSTRACT

A medical injector is provided herein having a body and a needle mounting surface movable relative to the body, the needle mounting surface having features for mounting a needle thereto. In an initial state, the needle mounting surface is disposed within the body with no needle mounted thereto. With relative movement between the body and the needle mounting surface, the needle mounting surface is urged out of the body. Advantageously, a medical injector is provided which ensures proper sequence in preparation of the device, particularly with respect to the step of allowing mounting of a medical needle to the device subsequent to preparation of the medicament to be administered.

6 Claims, 10 Drawing Sheets

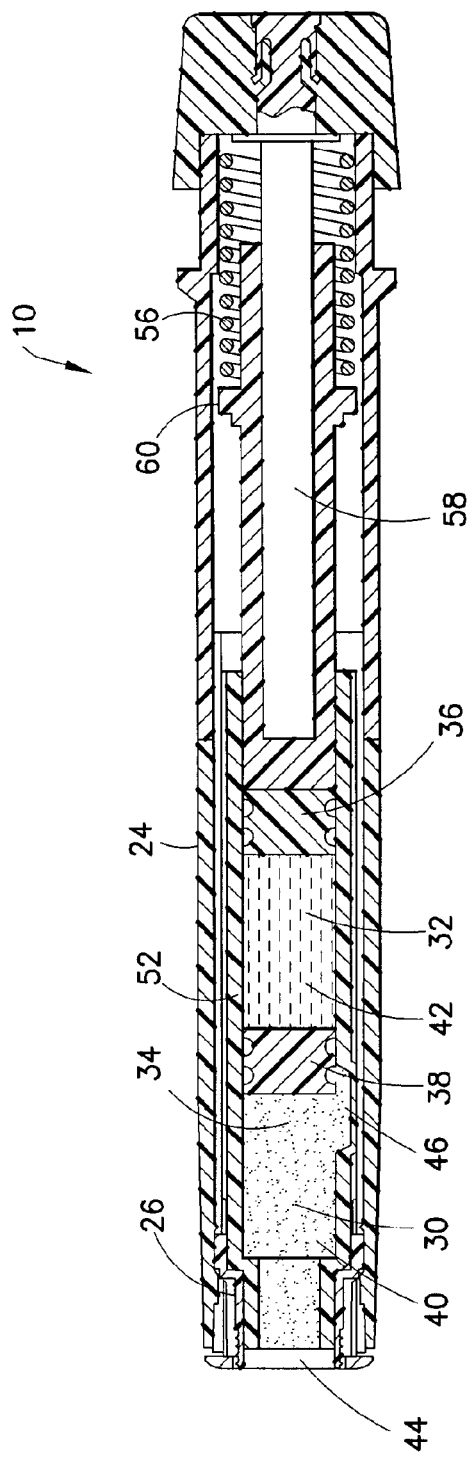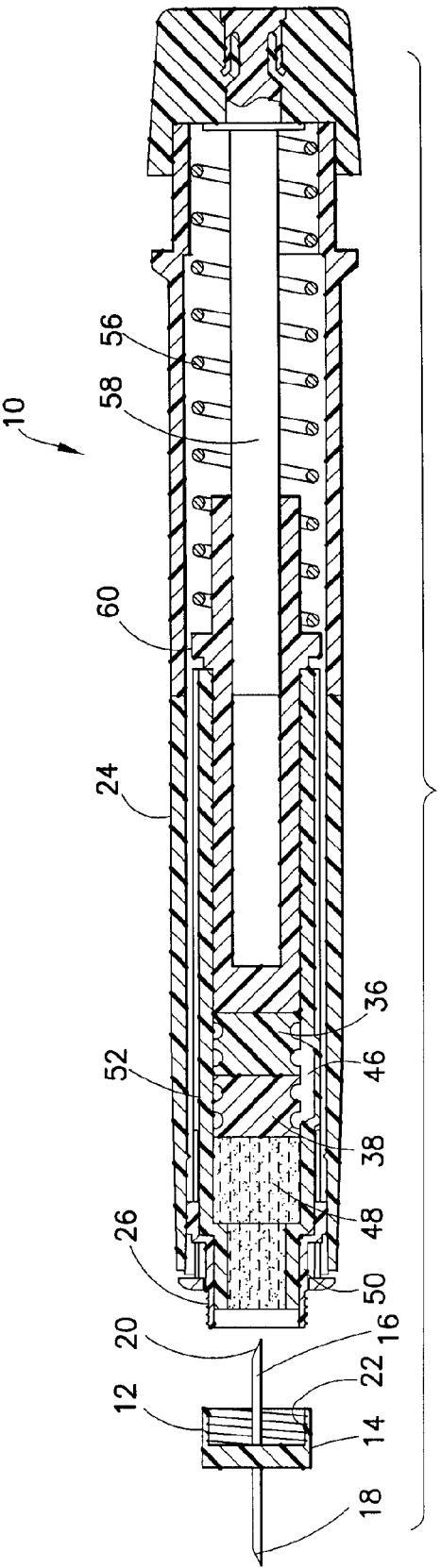

NEEDLE MOUNTING FEATURE FOR ENSURING PROPER RECONSTITUTION SEQUENCE

FIELD OF THE INVENTION

This invention relates to devices for reconstitution and, more particularly, to devices which ensure proper sequencing of reconstitution.

BACKGROUND OF THE INVENTION

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder form that require reconstitution.

In addition, drugs may be provided as multipart systems which require mixing prior to administration. For example, one or more liquid (e.g., flowable (slurry or liquid)) components, and/or dry (e.g., powdered or granular) components may be provided in a drug container or delivery device which require mixing prior to administration. The components can be mixed and used to form various administratable drugs, such as insulin.

Prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. U.S. Pat. No. 4,874,381 to Vetter is directed to an injector having a barrel configured for mixing, while U.S. Pat. No. 4,968,299 to Ahlstrand et al. is directed to a drug cartridge having a barrel configured for mixing. Both Vetter et al. and Ahlstrand et al. disclose typical configurations for mixing where a bypass channel is formed in the barrel of the device. As such, the device must be specifically configured for mixing.

Manual force may be applied to a reconstitution device to cause the mixing of the multiple components. In addition, autoreconstitution devices have been developed in the prior art which provide a trigger-activated automated reconstitution. U.S. Pat. No. 6,793,646 to Giambattista et al. is an example of an autoreconstitution device.

In typical reconstitution configurations, it is desired to have the components mixed prior to placing a needle in communication with the reservoir. Thus, with no needle being mounted to the device, the reservoir is not vented during mixing. It has been found that some individuals inadvertently mount a needle onto a device prior to reconstitution. This may result in improper mixing and/or inadvertent wasteful discharge through the needle.

It is noted that autoinjectors are known in the prior art which may also cause reconstitution. Autoinjectors, however, are trigger-activated devices which not only cause reconstitution, but will also cause a needle to pierce a patient's skin with subsequent automated plunger drive causing fluid administration. Autoinjectors typically do not have dose settings. In addition, the needle is pre-mounted to the device. Examples of this type of device may be found in U.S. Published Patent Application No. 2004/0133163 to Schiffmann and in U.S. Published Patent Application No. 2007/0142769 to Griffiths et al.

SUMMARY OF THE INVENTION

A medical injector is provided herein having a body and a needle mounting surface movable relative to the body, the needle mounting surface having features for mounting a needle thereto. In an initial state, the needle mounting surface is disposed within the body with no needle mounted thereto. With relative movement between the body and the needle mounting surface, the needle mounting surface is urged out of the body. Advantageously, a medical injector is provided which ensures proper sequence in preparation of the device, particularly with respect to the step of allowing mounting of a medical needle to the device subsequent to preparation of the medicament to be administered.

These and other features of the invention will be better understood through a study of the following detailed description and accompanying drawings.

BRIEF DESCRIPTION OF THE DRAWINGS

FIGS. 1 and 2 show a medical injector before and after reconstitution with altered states of a needle mounting surface;

DETAILED DESCRIPTION OF THE INVENTIION

Figure 3:
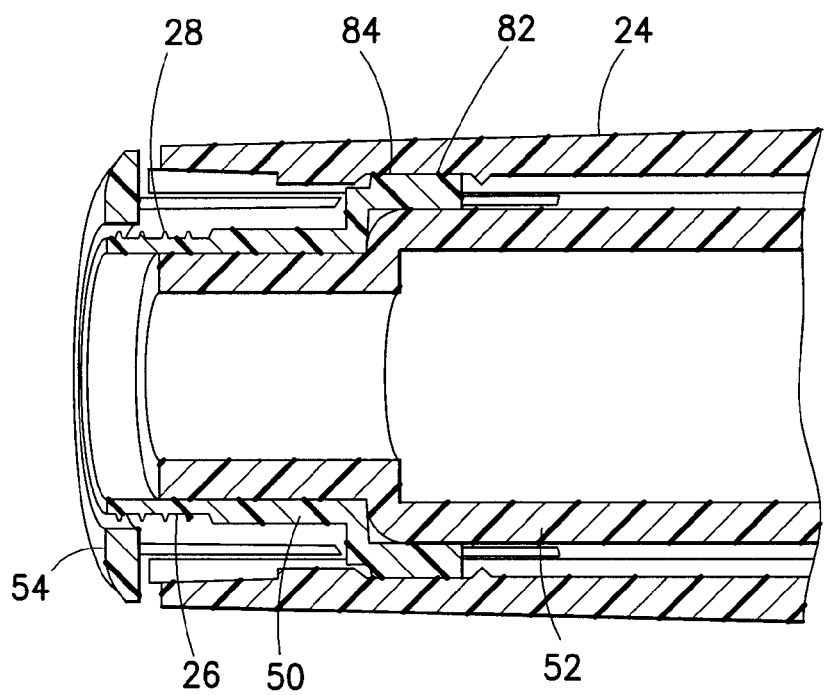
FIGS. 3 and 4 show altered states of a needle mounting surface.

With reference to the Figures, the subject invention provides a medical injector 10 which ensures proper sequence of preparation of the medical injector 10 for an injection. In particular, the medical injector 10 is configured to permit mounting of a needle 12 thereto only in proper sequence after reconstitution of mixable components contained in the medical injector 10. The medical injector 10 may be in the form of any medical injector, such as a syringe or pen injector, which is capable of reconstituting mixable components accommodated therein into an administrable liquid. The medical injector 10 may be also a fixed dose or variable dose injector (e.g., having a dose-setting mechanism). Further, the medical injector 10 may be a single- or multiple-dose device.

The needle 12 may be in any form. Preferably, the needle 12 includes a hub 14 to which is affixed a needle cannula 16. Distal end 18 of the needle cannula 16 is formed for insertion into a patient, while proximal end 20 may optimally be sharpened. The hub 14 may be formed with mounting features 22, such as threads, for mounting onto the medical injector 10, as described below.

As used herein, the term "distal", and derivatives thereof, shall refer to a direction toward a patient during use, while the term "proximal" and derivatives thereof, shall refer to a direction away from a patient during use.

The medical injector 10 includes a body 24 which may be formed of one or more components. The medical injector 10 also includes a needle mount or mounting surface 26 having features 28 for mounting the needle 12 thereto. The features 28 may be of any known type for mounting the needle 12 including features for creating a cooperating mechanical lock with the needle 12, particularly for cooperating with the mounting features 22, such as threads, bayonet lock members, detents, grooves, and so forth, and/or frictional engagement with the hub 14, such as through a tapered Luer configuration.

The medical injector 10 is a reconstitution device which, as shown in FIG. 1, includes at least first and second mixable components 30, 32 in an initial state. A reservoir 34 is disposed in the body 24 for accommodating the first and second mixable components 30, 32. At least one stopper 36 is associated with the reservoir 34 configured such that distal advancement of the stopper 36 over a predetermined distance shall cause mixing of the first and second mixable components 30, 32. Any known arrangement for allowing such mixing may be utilized. By way of non-limiting example, the first and second mixable components 30, 32 may be separated by a secondary stopper 38. The secondary stopper 38 divides the reservoir 34 into first and second chambers 40, 42, respectively, accommodating the first and second mixable components 30, 32. A septum 44 seals off the distal end of the first chamber 40, while the stopper 36 is positioned to seal off the proximal end of the second chamber 42. Preferably, if a dry component is used as one of the mixable components, the dry mixable component is located in the first chamber 40.

One or more by-pass channels 46 are formed in the wall of the reservoir 34. In an initial state, as shown in FIG. 1, the secondary stopper 38 is located at least partially proximally of the by-pass channels 46 so as to define a seal between the first and second chambers 40, 42 and to define a seal between the second chamber 42 and the by-pass channels 46. With distal advancement of the stopper 36, and with the second mixable component 32 being wet and generally incompressible, force of movement of the stopper 36 is transmitted to the secondary stopper 38 through the second mixable component 32. With sufficient distal movement of the secondary stopper 38, the second chamber 42 comes into communication with the by-pass channels 46, thus allowing the second mixable component 30 to be urged into the first chamber 40 with further distal movement of the stopper 36. With reference to FIG. 2, with sufficient distal advancement of the stopper 36, the second chamber 42 is collapsed with none or substantially none of the second mixable component 32 remaining therein. In addition, the secondary stopper 38 is located so as to define a seal between the first chamber 40 and the by-pass channels 46. The first and second mixable components 30, 32 are mixed within the first chamber 40, such as through agitation of the medical injector 10, so as to produce an injectable solution 48, ready for injection.

As will be recognized by those skilled in the art, other arrangements for permitting reconstitution may be utilized. In addition, more than two-part systems, such as three-part, and so forth, systems may be utilized. Active medical ingredients may be included in one or both of the first and second mixable components 30, 32. The first mixable component 30 may be dry (e.g., a powder or granular substance) and/or a liquid (e.g., flowable (slurry or liquid)). As mentioned above, the second mixable component 32 is preferably only a wet flowable component such as a liquid or slurry.

In a first embodiment, the needle mounting surface 16 may be defined on an adaptor 50 which is affixed to a drug cartridge 52 which houses the reservoir 34. The drug cartridge 52 is disposed in the body 24 so as to be movable relatively thereto. In an initial state, as shown in FIGS. 1 and 3, the drug cartridge 52 is located such that the needle mounting surface 26 is positioned within the body 24. In the initial state, the needle 12 is not mounted to the needle mounting surface 26. In addition, the location of the needle mounting surface 26 within the body 24 prevents mounting of the needle 12. It is preferred that the radial spacing between the needle mounting surface 26 and the surrounding portion of the body 24 be sufficiently minimized so as to prevent mounting of the needle 12 to the needle mounting surface 26. To this end, a shoulder 54 may be provided which extends radially inwardly from the body 24 at least partially about the circumference of the needle mounting surface 26.

Figure 4:
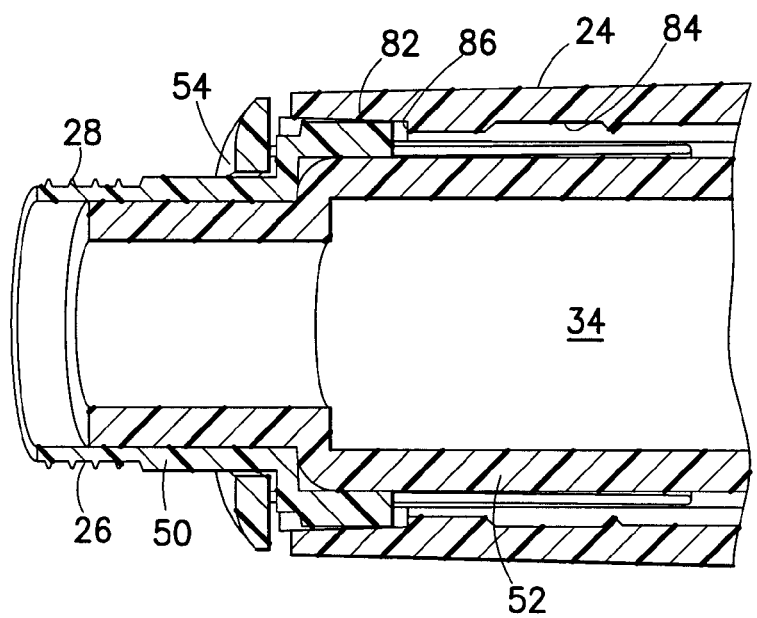

With reference to FIGS. 2 and 4, once the medical injector 10 is ready for use, relative movement between the body 24 and the drug cartridge 52, i.e., relative movement between the body 24 and the needle mounting surface 26, results in the needle mounting surface 26 extending from the body 24 ready for mounting of the needle 12 thereto. It is preferred that relative movement between the body 24 and the drug cartridge 52 be achieved during and/or after reconstitution of the first and second mixable components 30, 32 accommodated in the reservoir 34. In this manner, the needle mounting surface 26 is only made accessible once reconstitution has been initiated.

It is preferred that relative movement between the body 24 and the drug cartridge 52 be automated and more preferably occur during reconstitution. Various trigger-activated autoreconstitution configurations are known in the prior art, such as that disclosed in U.S. Pat. No. 6,793,646 to Giambattista et al., which is incorporated by reference herein in its entirety. As shown in U.S. Pat. No. 6,793,646, and with reference to FIGS. 1 and 2, a spring 56 may be provided to cause plunger 58 to drive forward. The plunger 58 acts against the stopper 36 in achieving autoreconstitution of the first and second mixable components 30, 32, as described above. The spring 56 may act, via the plunger 58 or other intermediate elements, to distally drive the drug cartridge 52 from the initial position shown in FIG. 1 to the second position shown in FIG. 2. A collar 60 may be provided on the plunger 58 which engages the drug cartridge 52 upon a predetermined extent of distal movement under force of the spring 56 with further distal advancement causing distal displacement of the drug cartridge 52 to the state shown in FIG. 2. The body 24 may act as a stop limiting distal advancement of the drug cartridge 52, such as by interengagement between the shoulder 54 and the drug cartridge 52.

The spring 56 is retained in the first position of FIG. 1 by any known manner of retaining mechanism. A trigger may be provided to release the retaining mechanism to cause autoreconstitution and advancement of the drug cartridge 52.

Reconstitution of the first and second mixable components 30, 32 is conducted without the needle 12 mounted to the medical injector 10. As such, the reservoir 34 is not vented during the mixing. With the needle 12 being mounted to the medical injector 10 after the mixing, any residual gases trapped in the reservoir 34 are purged through the needle 12. It may be preferred to not provide a physical stop to the distal advancement of the plunger 58 during reconstitution. In this manner, the mixed components may be maximally compressed under force of the spring 56. With mounting of the needle 12 onto the medical injector 10, the reservoir 34 is vented thus permitting further distal advancement of the plunger 58. This secondary distal advancement may assist in priming a needle for use. The physical stop (e.g., the shoulder 54) may be located to engage the drug cartridge 52 after the secondary distal advancement.

Figure 5:
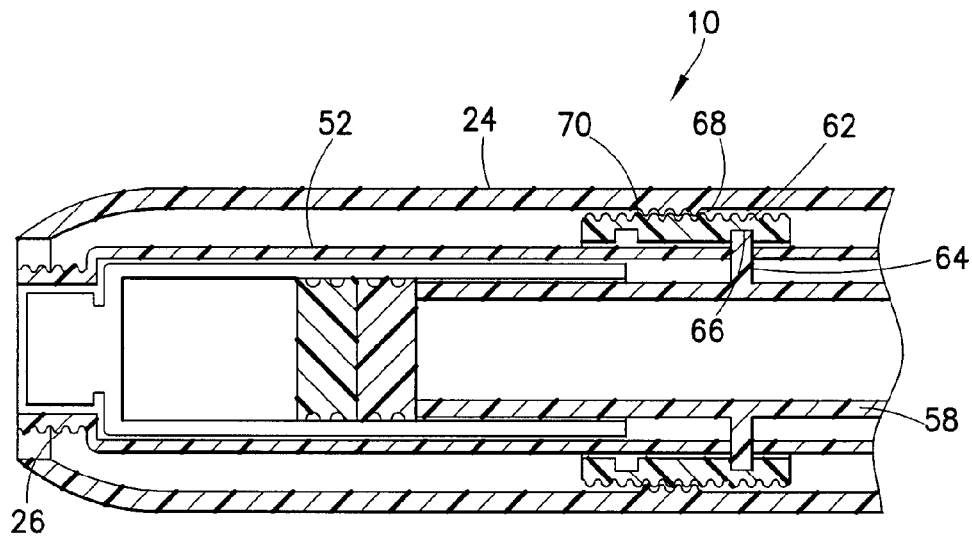
FIGS. 5 and 6 show an arrangement for generating relative movement between a drug cartridge and body of a medical injector.
Figure 6:
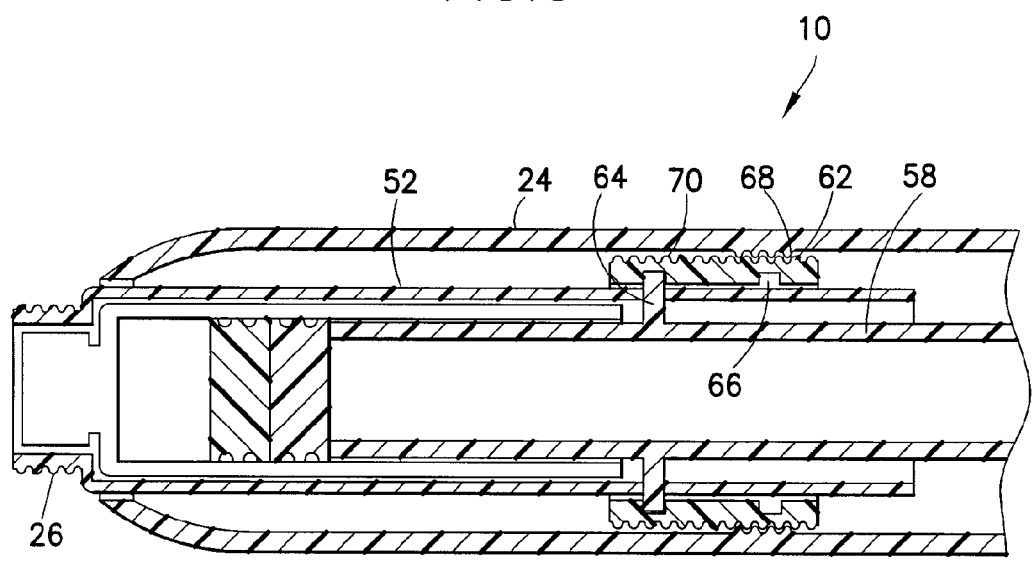

As will be appreciated by those skilled in the art, relative motion between the body 24 and the drug cartridge 52 may be caused by movement of one or both of the components. With reference to FIGS. 1 and 2, the drug cartridge 52 is displaced relative to the body 24. Other arrangements are useable with the subject invention. With reference to FIGS. 5 and 6, for example, a configuration is shown where the body 24 is displaced relative to the drug cartridge 52. As shown, an intermediate threaded collar 62 is located between the drug cartridge 52 and the body 24. In addition, a large thread 64 is located on the plunger 58 formed to engage a cooperating thread 66 located inside the threaded collar 62. Body thread 68 is located to engage outer thread 70 formed on the outer portion of the threaded collar 62. It is preferred that the pitch of the cooperating thread 66 be relatively steep while the pitch of the outer thread 70 be relatively shallow, i.e., not steep (pitch of the cooperating thread 66 is steeper than the pitch of the outer thread 70). The plunger 58 is also non-rotatably disposed in the medical injector 10. With this arrangement, distal advancement of the large thread 64 will cause the threaded collar 62 to rotate about the plunger 58 resulting in retraction of the body 14 relative to the drug cartridge 52. As shown in FIGS. 5 and 6, this results in the needle mounting surface 26 extending from the body 24 ready for use. The plunger 58 may be driven by the spring 56.

Figure 7:
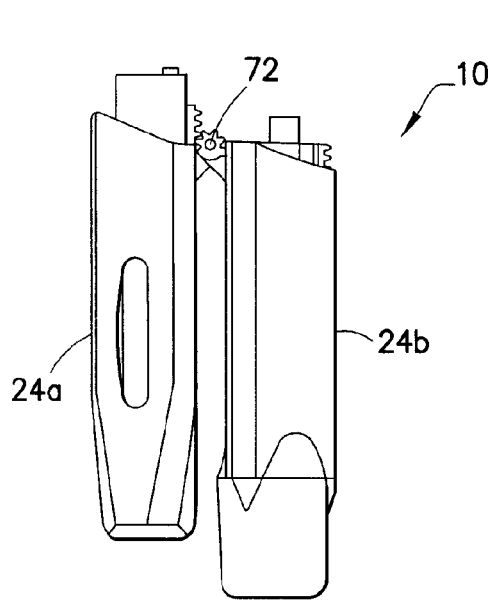
FIGS. 7-11 show an alternative arrangement for generating relative movement between a drug cartridge and body of a medical injector.
Figure 9:
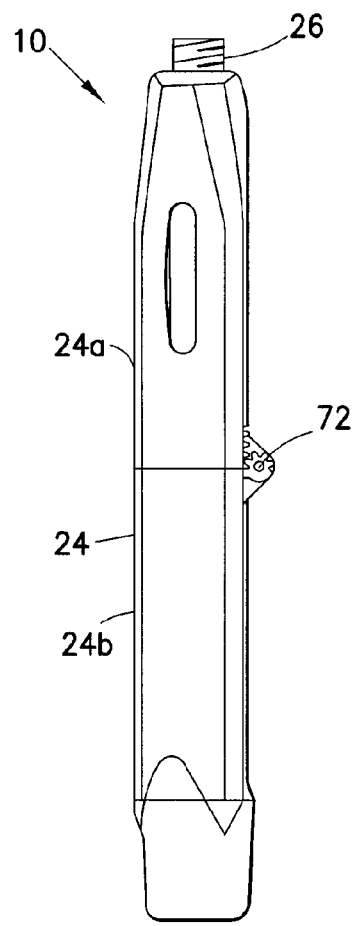
Figure 8:
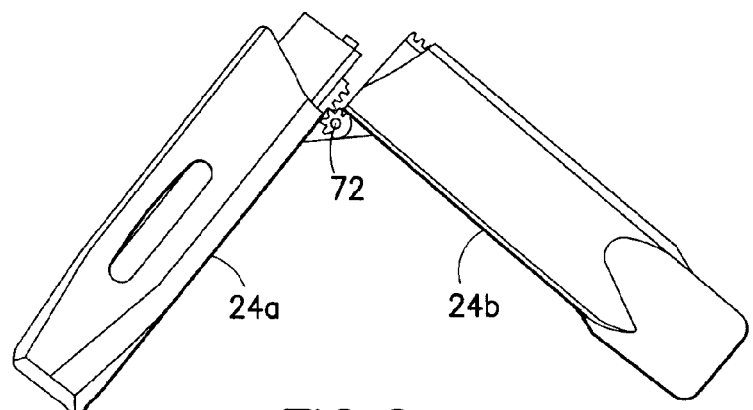

With reference to FIGS. 7-11, the drug cartridge 52 may be caused to move under mechanical force applied to the medical injector 10. By way of non-limiting example, and with reference to FIGS. 7-11, the body 24 may be provided as two components 24a, 24b which are pivotally connected through a hinge connection 72. The components 24a, 24b are caused to rotate about the hinge connection 72 to snap together in forming the body 24, as shown in FIGS. 7-9. The component 24a may house the drug cartridge 52. The components 24a, 24b may be configured such that assembly of the components 24a, 24b triggers reconstitution of the contents of the drug cartridge 52. Such a snap together reconstitution arrangement is disclosed in copending Application No. PCT/US2009/057446, the entire contents of which are incorporated by reference herein.

As will be appreciated by those skilled in the art, various modes of providing force for moving the needle mounting surface 26 may be provided. Utilizing force from an autoreconstitution configuration is preferred, such as force from a drive spring and/or force imparted to the medical injector. In addition, manual force may be applied directly to the plunger 58 for manual reconstitution which is also utilized to displace the needle mounting surface 26.

Figure 10:
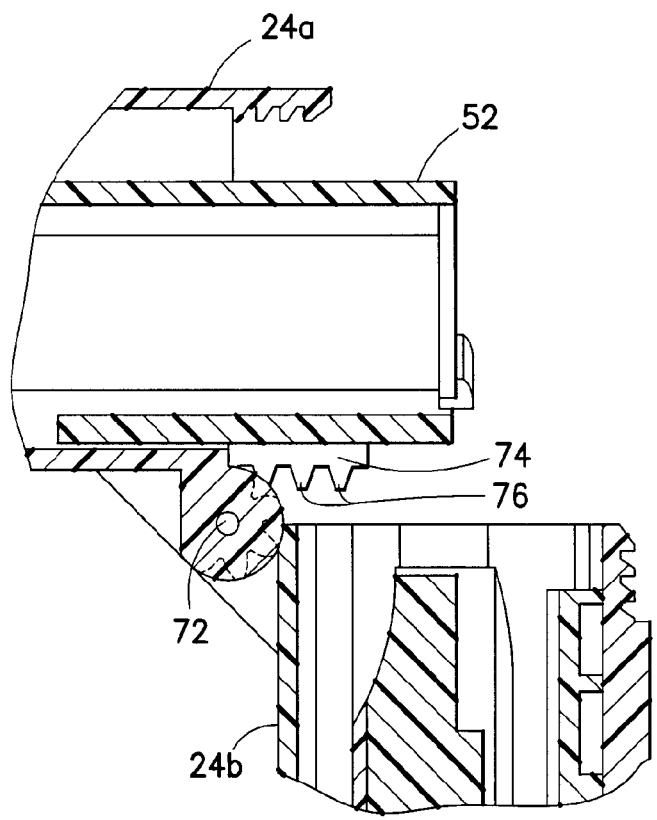
Figure 11:
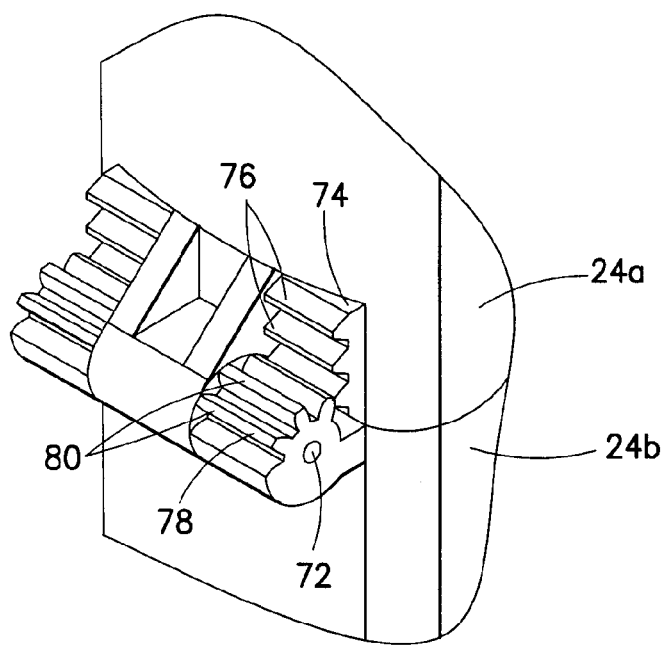

In addition, as shown in FIGS. 10-11, a rack 74 having a plurality of teeth 76 may be formed on the drug cartridge 52. The hinge connection 72 may include a pinion 78 having a plurality of pinion teeth 80 formed to mesh with and engage the teeth 76. Thus, with rotation of the components 24a, 24b about the hinge connection 72, the pinion 78 engages the rack 74 with the teeth 76 being in meshing engagement with the pinion teeth 80. Rotation of the pinion 78 results in linear translation of the rack 74 resulting in distal advancement of the drug cartridge 52 relative to the body 24. As shown in FIG. 9, the needle mounting surface 26 is thus caused to extend from the body 24.

It is further preferred that a releasable retaining arrangement be provided for releasably retaining the needle mounting surface 26 prior to displacement of the drug cartridge 52 to minimize inadvertent displacement. With reference to FIGS. 3 and 4, the releasable retaining arrangement may include a cooperating rib 82 and groove 84 arrangement where the rib 82 nests in the groove 84 to provide retention. As shown in the Figures, it is preferred that the rib 82 be formed on the adaptor 50 and the groove 84 be formed in the body 24, but the reverse relationship is also useable. Thus, with initial application of motive force to the drug cartridge 52, a threshold amount of resistance must be overcome to dislodge the drug cartridge 52 from the releasable retaining arrangement to permit distal advancement.

It is further preferred that a locking arrangement be provided to lock the needle mounting surface 26 in the extended state. With reference to FIG. 4, a secondary stop 86 may be formed on the body 24 configured to resist proximal movement of the needle mounting surface 26 once extended. In addition, the shoulder 54 may be formed to resist distal movement. The combination of the shoulder 54 and the secondary stop 86 may provide a locking effect to the needle mounting surface 26 in the extended state.

Figure 12:
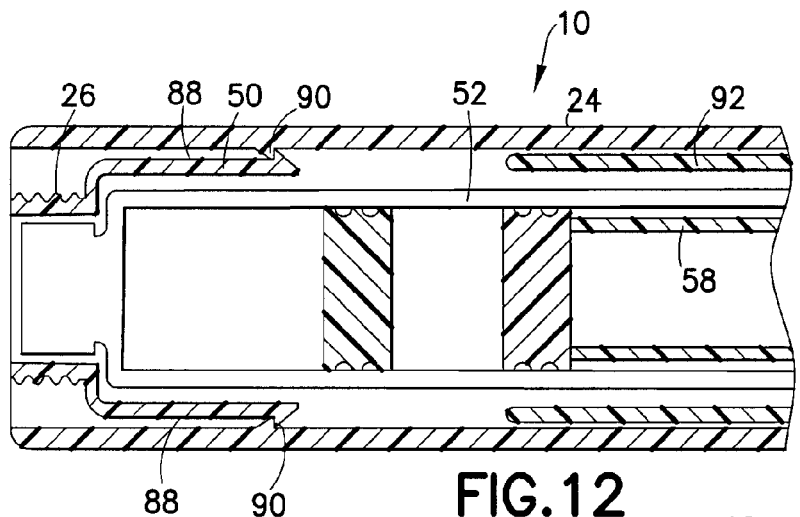
FIGS. 12-14 show releasable retaining and locking arrangements for a needle mounting surface.
Figure 13:
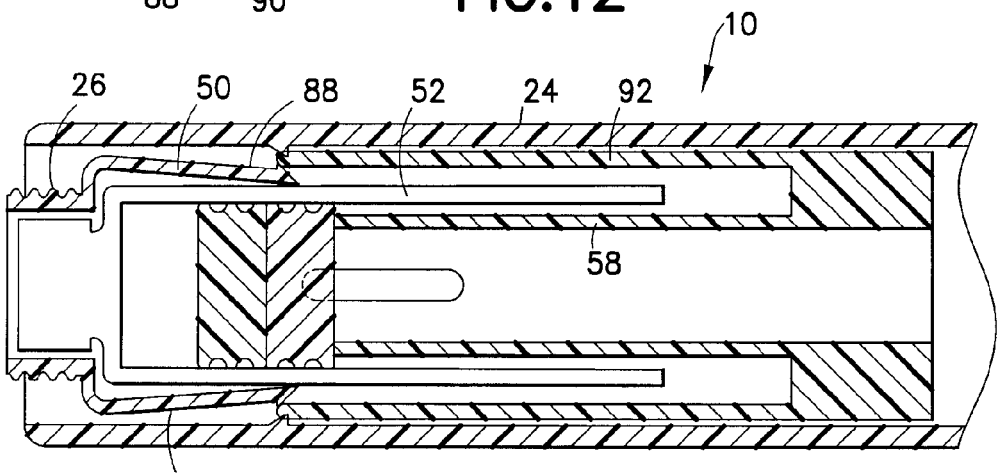
Figure 14:
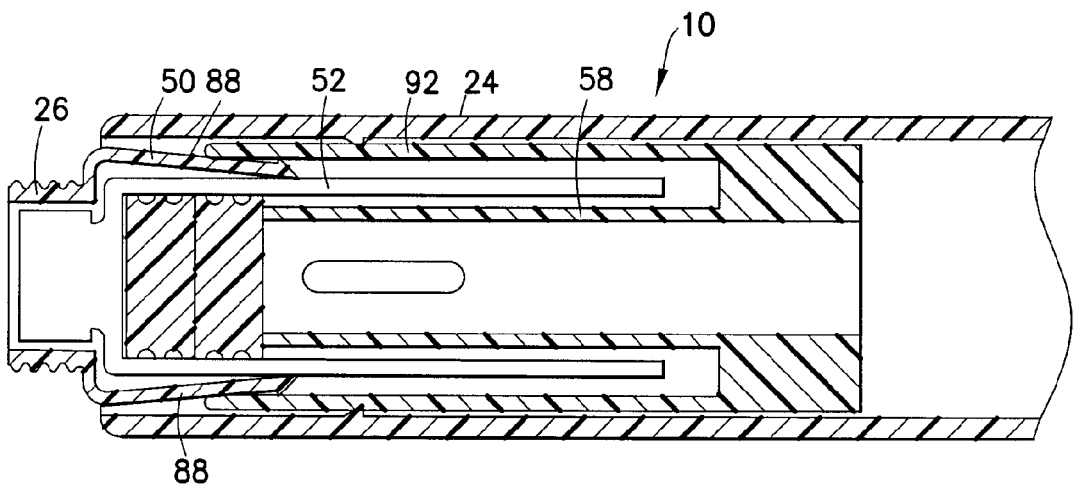

As will be appreciated by those skilled in the art, other retaining and locking arrangements are useable with the subject invention. With reference to FIGS. 12-14, the adaptor 50 may be provided with one or more deflectable arms 88 releasably retained by catches 90 formed on the body 24. The plunger 58 may be formed with an outer release member 92 which distally advances with the plunger 58 during reconstitution. As shown in FIG. 13 with sufficient distal movement, the release member 92 engages the arms 88 causing inward deflection thereof and release from the catches 90 thereby allowing the needle retaining surface 26 to distally advance to the extended state outside of the body 24. The arms 88, the release member 92 and the body 24 are configured such that the release member 92 may be tightly wedged between the arms 88 and the body 24 in a post-reconstitution state in creating a locking effect for the needle mounting surface 26 in the extended state.

Figure 15:
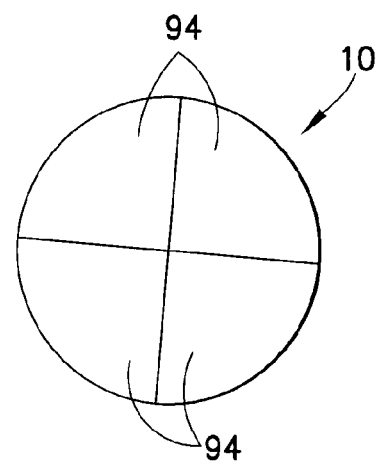
FIGS. 15-18 show an arrangement of separable leaves useable with the subject invention.
Figure 16:
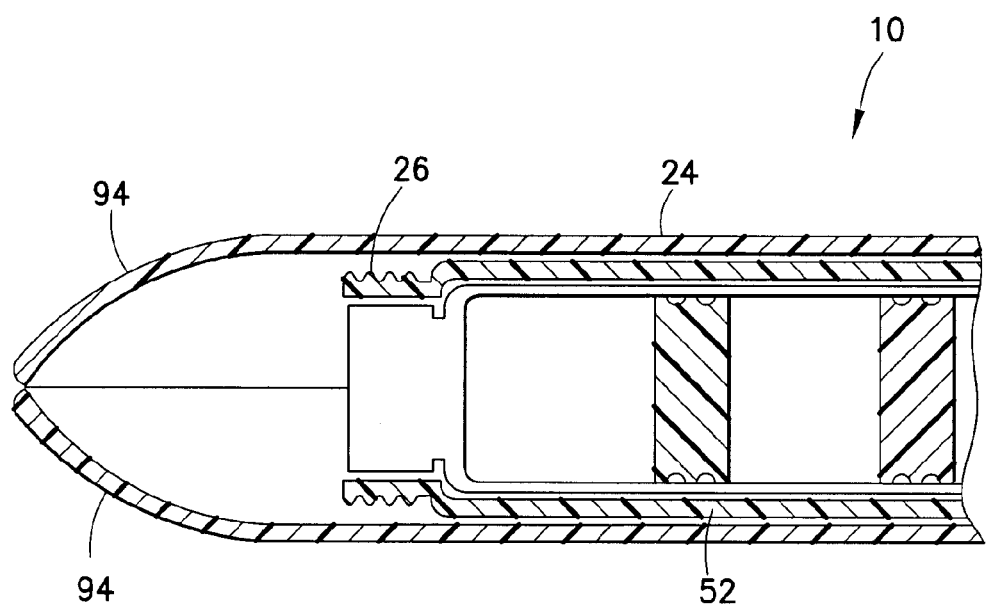
Figure 17:
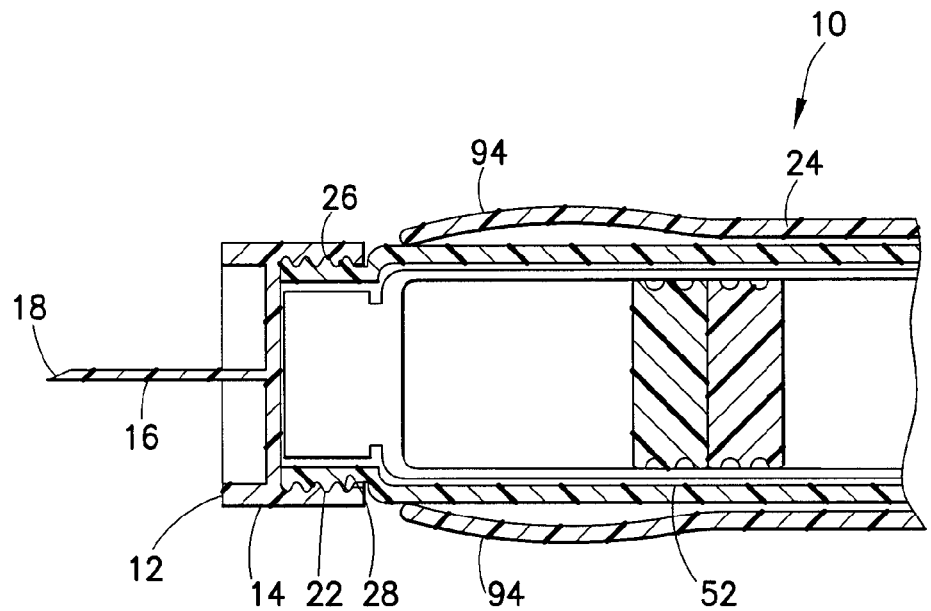

As shown in FIGS. 1-4, the distal end of the medical injector 10 may be partially opened. With reference to FIGS. 15-18, the distal end may be defined by a plurality of spreadable leaves 94. The leaves 94 are resilient and inherently biased to a closed state, as shown in FIGS. 15 and 16. With relative movement between the drug cartridge 52 and the body 24, the leaves 94 may be spread open (FIG. 17) with the needle mounting surface 26 extending therefrom allowing the needle 12 to be mounted thereto.

Figure 18:
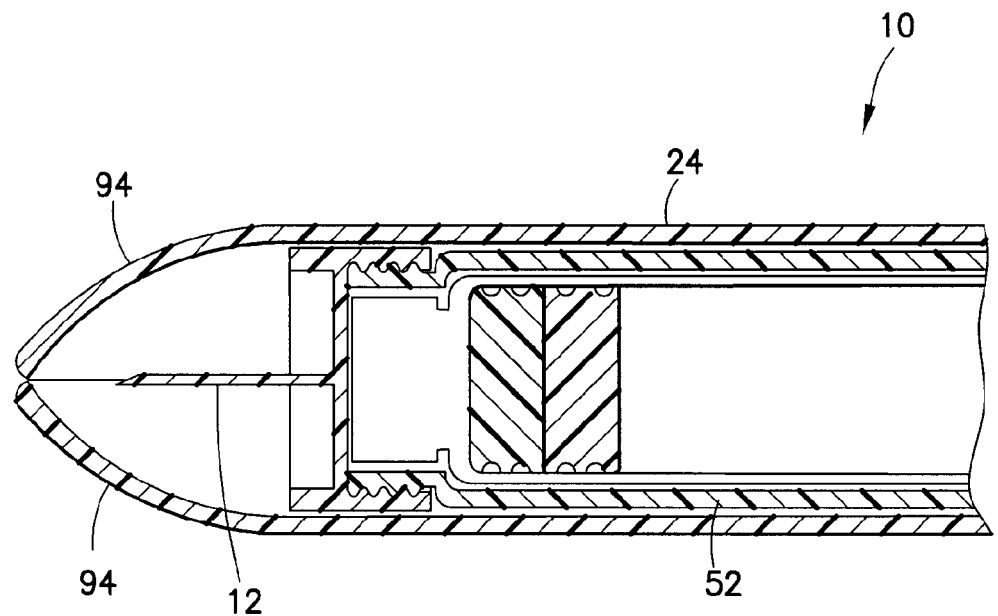

In addition, if reverse relative movement between the body 24 and the drug cartridge 52 is achievable (e.g., no locking configuration is provided to lock the needle retaining surface 26 in the extended state), the needle retaining surface 26 can be caused to be contained within the body 24 after use. As shown in FIG. 18, with the needle 12 being mounted to the medical injector 10, the leaves 94 may close again, thus shielding the needle 12 in a used state.

Figure 19:
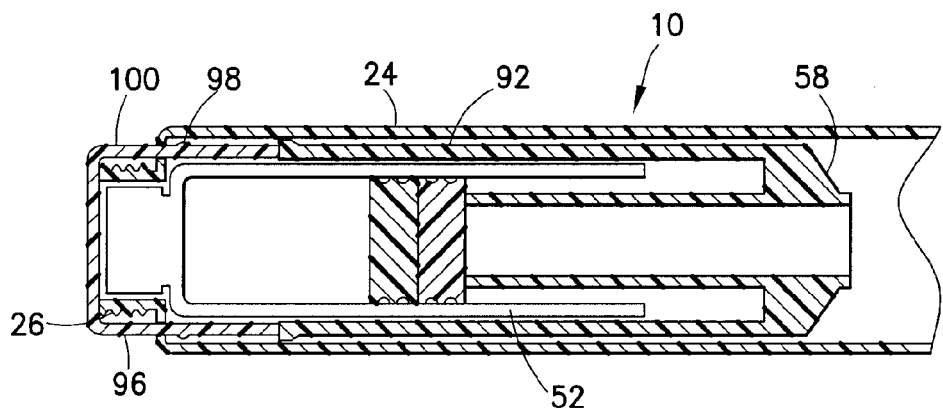
FIGS. 19-21 show a second embodiment of the subject invention utilizing a releasably attached overcap; and, FIGS. 22-24 show a third embodiment of the subject invention utilizing a slidable collet and outwardly biased resilient members.
Figure 20:
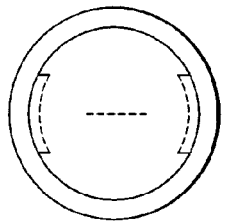
Figure 21:
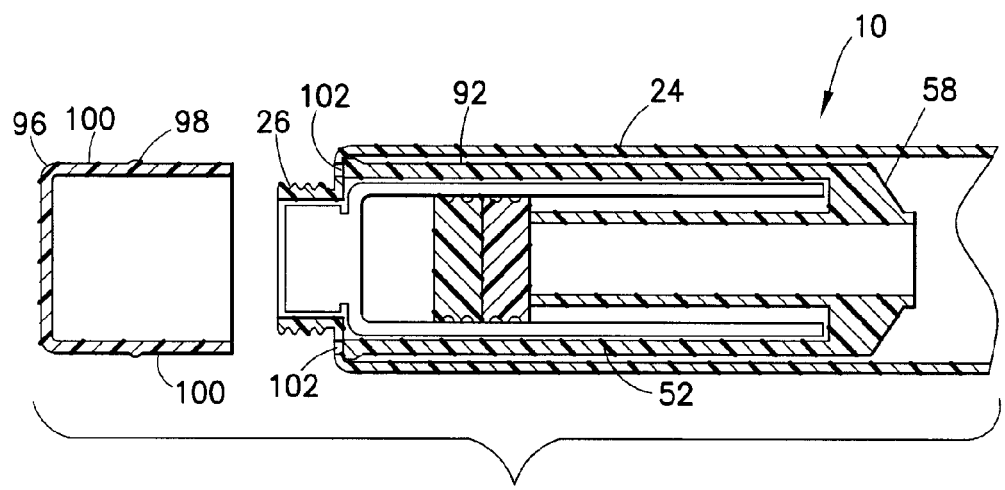

In a second embodiment of the invention, a secondary element may be used to cover the needle mounting surface 26 so as to prevent a needle from being mounted thereto prior to reconstitution. With the secondary element being released upon reconstitution, a needle may be mounted to the needle mounting surface 26. With reference to FIGS. 19-21, an overcap 96 may be releasably attached to the body 24 and configured to cover the needle mounting surface 26 prior to reconstitution so as to prevent a needle from being mounted thereto. In particular, the overcap 96 is cup-shaped so as to encompass the needle mounting surface 26 with one or more protrusions 98 being formed on protruding sidewalls 100. The sidewalls 100 extend through one or more apertures 102 formed in the shoulder 54 of the body 24. The protrusions 98 are located within the body 24 and proximally of the apertures 102. The protrusions are sized so as to provide resistance against removal of the overcap 96 from the body 24. As shown in FIG. 21, with the plunger 58 having the release member 92, sufficient distal advancement of the plunger 58 results in the overcap 96 being urged distally with the protrusions 98 becoming clear of the apertures 102, thus releasing the overcap 96. In this manner, the overcap 96 may be released upon reconstitution. Once the overcap 96 is released from the body 24, the needle mounting surface 26 is free to have a needle mounted thereto.

Figure 22:
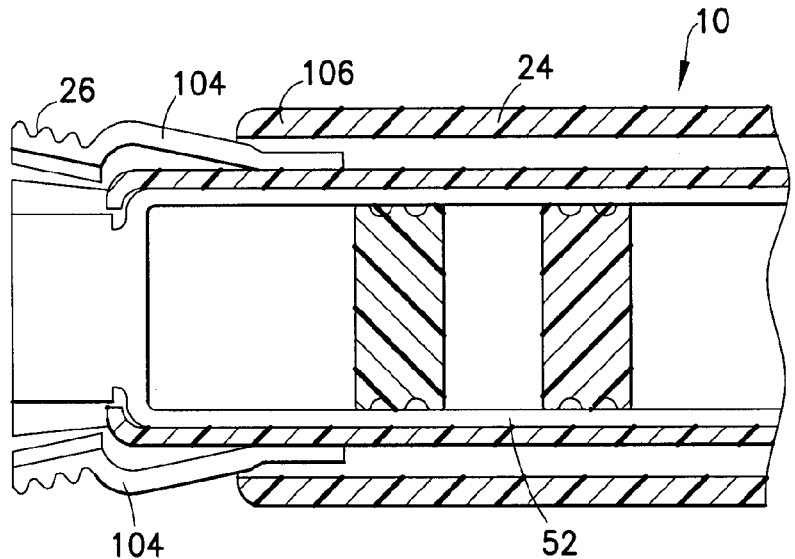
Figure 23:
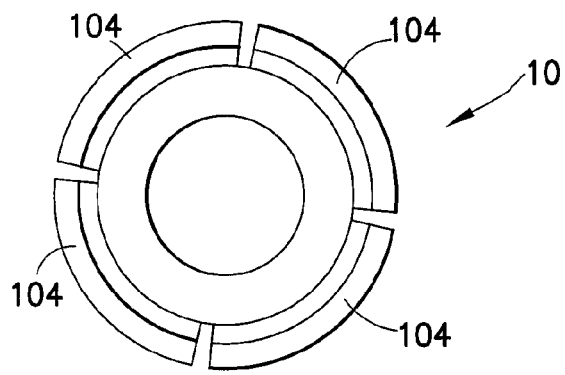
Figure 24:
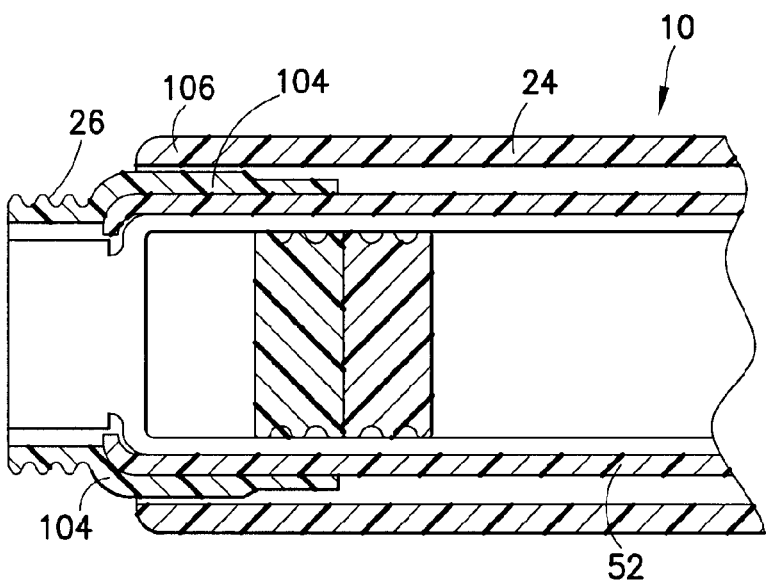

In a third embodiment of the subject invention, a medical injector 10 may be configured such that the needle mounting surface 26 may be provided in an initial state where a needle can not be mounted thereto with a subsequent change of state resulting in the needle mounting surface 26 being utilizable with a needle. With reference to FIGS. 22-24, the needle mounting surface 26 may be defined by a plurality of resilient members 104 which are inherently biased outwardly. The resilient members 104 are sufficiently biased outwardly so as to form a disrupted state for the needle mounting surface 26 which is unuseable for mounting a needle thereto. The resilient members 104 are deflectable inwardly so as to collectively define the needle mounting surface 26 in a usable state, as shown in FIG. 24. Inward deflection of the resilient members 104 may be achieved by a slidable collet 106 that may be a separate element or defined by the body 24. With reference to FIGS. 22 and 24, distal advancement of the collet 106 relative to the resilient members 104 causes inward deflection thereof and, thus, defines the needle mounting surface 26 in a useable state. Distal advancement of the collet 106 may be achieved upon reconstitution utilizing any of the configurations discussed above.

What is claimed is:

1. A medical injector comprising:
   a body having proximal and distal ends; and,
   a needle mount movable relative to said body, said needle mount having features for mounting a needle thereto,
   wherein, in an initial state, said needle mount being disposed within said body with no needle mounted thereto, and
   wherein, with relative movement between said body and said needle mount, said needle mount is urged through a portion of said body and then out of said body, past said distal end, to extend from said distal end in an extended state.

2. A medical injector as in claim 1, further comprising locking means for locking said needle mount in said extended state.

3. A medical injector as in claim 1, further comprising a plurality of spreadable leaves, said leaves being inherently biased to a closed state, wherein, upon said relative movement between said body and said needle mount, said needle mount passes through said leaves to said extended state.

4. A medical injector as in claim 1, further comprising a drug cartridge disposed in said body, said needle mount being defined thereon, said drug cartridge being movable relative to said body.

5. A medical injector as in claim 4, further comprising a releasable retainer for retaining said needle mount within said body.

6. A medical injector as in claim 4, wherein said drug cartridge accommodates at least two mixable components, wherein, in said initial state, said mixable components being separate, and, wherein, said relative movement between said body and said needle mount being achieved with mixing of said mixable components.

\* \* \* \* \*